US012766304B2

(12) United States Patent
Laffay et al.

(10) Patent No.: US 12,766,304 B2
(45) Date of Patent: Oct. 20, 2026

(54) CLOSING ELEMENT FOR A FLUID LINE

(71) Applicant: FRESENIUS MEDICAL CARE DEUTSCHLAND GMBH, Bad Homburg (DE)

(72) Inventors: Philippe Laffay, Sainte Foy les Lyon (FR); Francois Dumont-D'ayot, Lyons (FR); Benoit Luaire, Sourcieux les Mines (FR); Winfried Brehm, Hofheim (DE); Martin Kaiser, Hassfurt (DE); Paul Seit, Schweinfurt (DE); Rafael Sterzer, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 707 days.

(21) Appl. No.: 18/024,781

(22) PCT Filed: Sep. 10, 2021

(86) PCT No.: PCT/EP2021/074973
§ 371 (c)(1),
(2) Date: Mar. 6, 2023

(87) PCT Pub. No.: WO2022/053635
PCT Pub. Date: Mar. 17, 2022

(65) Prior Publication Data

US 2024/0261560 A1 Aug. 8, 2024

(30) Foreign Application Priority Data

Sep. 11, 2020 (EP) .................................... 20195804

(51) Int. Cl.

| | |
|---|---|
| ***A61M 39/26*** | (2006.01) |
| ***A61M 1/16*** | (2006.01) |
| ***A61M 39/10*** | (2006.01) |

(52) U.S. Cl.
CPC .......... *A61M 39/26* (2013.01); *A61M 1/1666* (2014.02); *A61M 39/10* (2013.01)

(58) Field of Classification Search
CPC .... A61M 39/221; A61M 39/26; A61M 39/14; A61M 2039/1072; A61M 2039/1061
See application file for complete search history.

(56) References Cited

U.S. PATENT DOCUMENTS

| | | | | |
|---|---|---|---|---|
| 4,022,205 A * | 5/1977 | Tenczar | F16L 37/30 | 285/21.2 |
| 5,221,267 A * | 6/1993 | Folden | A61M 1/285 | 604/905 |

(Continued)

FOREIGN PATENT DOCUMENTS

| | | |
|---|---|---|
| CN | 111372631 A | 7/2020 |
| CN | 217938795 U | 12/2022 |

(Continued)

OTHER PUBLICATIONS

Office Action issued in corresponding Taiwan Patent Application No. 110133579 dated Jan. 8, 2025 (16 pages).

(Continued)

*Primary Examiner* — Adam Marcetich
*Assistant Examiner* — Ted Yang
(74) *Attorney, Agent, or Firm* — Kilyk & Bowersox, P.L.L.C.

(57) ABSTRACT

The present invention relates to a closing element for a fluid line, preferably a fluid line of a concentrate container, comprising a closing portion configured to be arranged on an end portion of the fluid line to fluidically close the fluid line, wherein the closing portion comprises an intended breaking point, and a pressure receiving portion configured to receive pressure applied by a connector element to be fluidically connected to the fluid line by breaking the intended breaking point, wherein the pressure receiving portion comprises at (Continued)

least one protrusion projecting outwards from at least a part of the closing element that is configured to come into contact with the connector element.

20 Claims, 7 Drawing Sheets

(56) References Cited

U.S. PATENT DOCUMENTS

| | | | | |
|---|---|---|---|---|
| 5,534,228 | A * | 7/1996 | Wesseler | A61M 39/10 604/416 |
| 9,707,337 | B2 | 7/2017 | O'Connor et al. | |
| 11,033,676 | B2 | 6/2021 | Dechelette et al. | |
| 2002/0072714 | A1 | 6/2002 | Epstein et al. | |
| 2003/0030272 | A1 | 2/2003 | Johnson et al. | |
| 2006/0074386 | A1* | 4/2006 | Wollmann | B01F 33/5011 604/246 |
| 2008/0132876 | A1* | 6/2008 | Felt | A61M 39/18 604/411 |
| 2013/0060233 | A1 | 3/2013 | O'Connor et al. | |
| 2014/0213975 | A1 | 7/2014 | Clemente et al. | |
| 2015/0217104 | A1* | 8/2015 | Biehl | A61M 39/18 604/500 |
| 2018/0143042 | A1 | 5/2018 | Damren et al. | |
| 2018/0296819 | A1* | 10/2018 | Chiang | A61M 39/162 |
| 2019/0111204 | A1 | 4/2019 | Booth et al. | |
| 2019/0167895 | A1 | 6/2019 | Dechelette et al. | |
| 2020/0315918 | A1* | 10/2020 | Naygauz | A61M 5/286 |
| 2024/0261560 | A1 | 8/2024 | Laffay et al. | |

FOREIGN PATENT DOCUMENTS

| | | | |
|---|---|---|---|
| WO | 2008070220 | A1 | 6/2008 |
| WO | 2019243044 | A1 | 12/2019 |

OTHER PUBLICATIONS

International Search Report and Written Opinion issued in corresponding International Patent Application No. PCT/EP2021/074973 mailed Nov. 11, 2021 (9 pages).

Office Action issued in corresponding Chinese Patent Application No. 202180061833.7 dated Jan. 30, 2026 (24 pages).

Office Action issued in corresponding Columbian Patent Application No. 19995 dated Nov. 11, 2025 (16 pages).

* cited by examiner

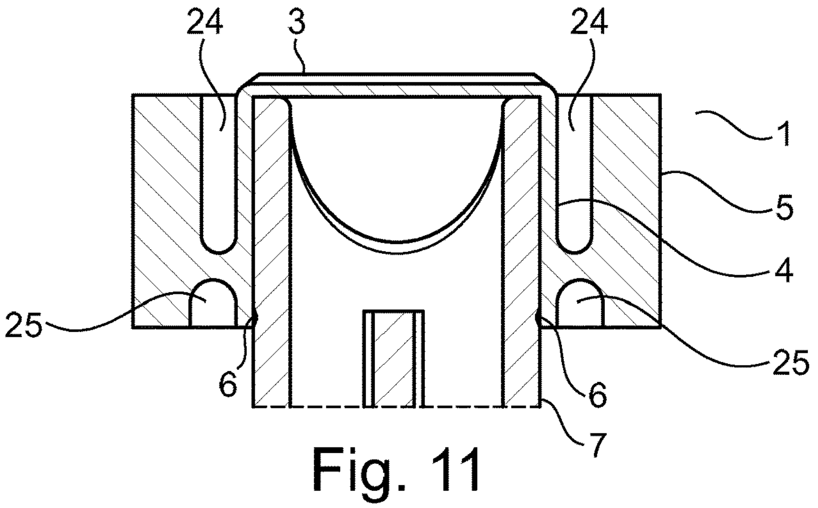
Fig. 11
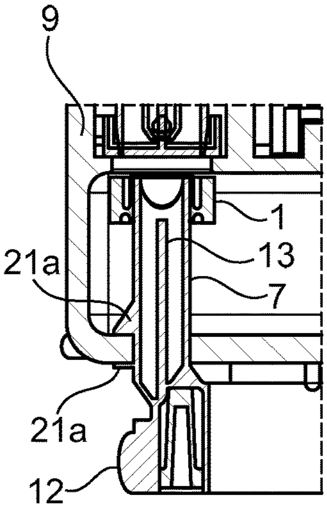
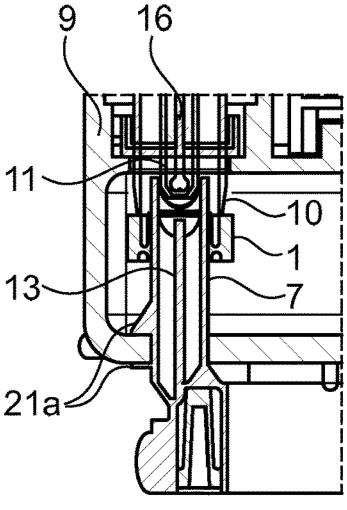
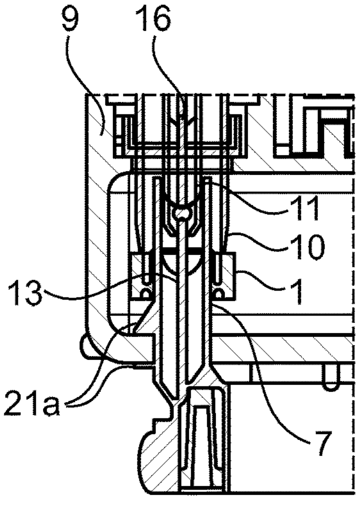
Fig. 12
Fig. 13
Fig. 14
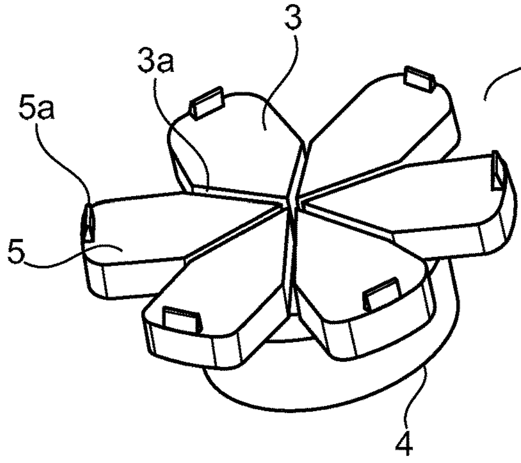
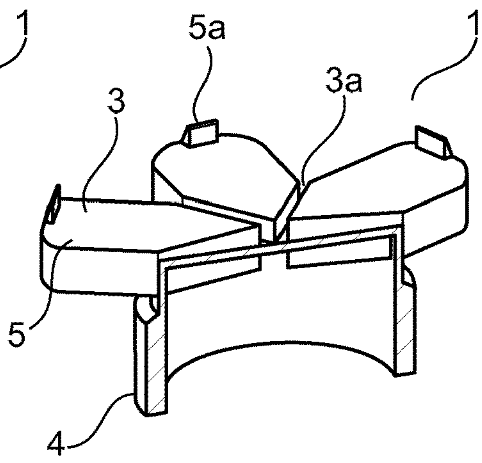
Fig. 15
Fig. 16

CLOSING ELEMENT FOR A FLUID LINE

This application is a National Stage Application of PCT/EP2021/074973, filed Sep. 10, 2021, which claims priority to European Patent Application No. 20195804.8, filed Sep. 11, 2020.

The present invention relates to a closing element for a fluid line, e.g. of a concentrate container for medical purposes, a connector comprising a fluid line closed by such a closing element and a system comprising a concentrate container having such a connector that is closed by such a closing element and a connector of a blood treatment device or dosing unit thereof.

In the process of blood treatment, e.g. a dialysis treatment, the required dialysis solution is often produced from dry concentrate that is mixed with pure water. For this purpose, containers containing a concentrate, e.g. bicarbonate or an acidic concentrate, are fluidically connected to the blood treatment device or a dosing unit thereof to allow mixing of a solution of a desired concentrate concentration.

Prior to connection of the container to the blood treatment device or dosing unit, the concentrate containers are sealed for storage. Prior to fluidically connecting the container to the blood treatment device or dosing unit, conventionally a seal is manually removed from the fluid lines of the concentrate container to open the fluid lines for the connection to corresponding connector elements of the blood treatment device. Thus, conventionally there is a significant risk of contamination due to extensive manual handling of the concentrate container. In addition to that, the film conventionally used for sealing the containers may easily be dislodged during storage of the container leading to a potentially contaminated and thus unusable container.

Another common approach to close medical containers which have to be fluidly connected to another fluid line for delivering the content to a treatment machine or a patient are closures with intended breaking edges. These closures do not have to be removed before use, but the connection is established by a part, for example a spike, which is introduced into the closing element having an intended breaking point. This has the disadvantage, that the part for establishing the connections firstly touches the outer surface of the closure, which can be contaminated.

It is an object of the present invention to alleviate or even overcome the problems of the prior art.

In particular, it is an object of the present invention to introduce a system that can be opened from the outside while being sure there is no contact between the outside and the product content.

Thereby a safe, reliable and hygienic means for fluidically closing a concentrate container, especially in a case in that the concentrate container is not directly manually opened but opened by the blood treatment device or dosing unit thereof, e.g. by manual movement of a connector element of the blood treatment device or dosing unit thereof, prior to connection thereto is provided. Especially in case of a manual connection of the concentrate container to the blood treatment device or dosing unit thereof, it is important to ensure that only a minimal amount of force is required for connecting. This reduces the strain on personnel that in daily practice has to perform such a connection day-to-day with a high frequency.

This object is achieved by the invention as recited in the independent claims. Advantageous embodiments of the invention are the subject-matter of the dependent claims.

A first aspect of the invention relates to a closing element for a fluid line, preferably a fluid line of a concentrate container, comprising:

- a main body configured to at least partially receive the fluid line,
- a closing portion configured to be arranged on an open portion of the fluid line to fluidically close the fluid line, wherein the closing portion comprises an intended breaking point, and
- a pressure receiving portion configured to receive pressure applied by a pressure exertion element, preferably a connector element to be fluidically connected to the fluid line by breaking the intended breaking point, wherein
- the pressure receiving portion comprises at least one protrusion, preferably projecting outwards from the closing portion or the main body, that is configured to come into contact with the connector element.

Preferably, the intended breaking point is an area of weakened material, e.g. a local thinning of the material. The intended breaking point can have the shape of a line or multiple lines. The closing portion can comprise one, two or more sections, e.g. having the shape of plates, that are separated from each other by one or more intended breaking points.

Alternatively or additionally, the intended breaking point may be manufactured from a material that is easier to break than the material from that the rest of or a part of the rest of the closing element. In this case, the closing element may be manufactured from at least two components. In the most general form, the closing element may be manufactured from two different components that are different from each other in their mechanical properties, in particular, one component is easier to break than the other component. Preferably, both components are polymers.

The targeted use of a polymer that is easy to break to selectively form areas of the closing element that are intended to be broken, such as the intended breaking point, offers the advantage that loess force is required to break the intended breaking point and thereby open the closing element.

For example, the closing element may be partially manufactured from a thermoplastic elastomer forming e.g. the breaking point and another polymer, e.g. a linear low density polyethylene (LLDP), forming the rest of the closing element.

During manufacture, for example, in a first step the part of the closing element to be made from the other polymer, e.g. a linear low density polyethylene (LLDP), first manufactured with gaps in the position of the portions to be manufactured from the material that is easier to break, e.g. the intended breaking point to be made from a thermoplastic elastomer. This first step gives rise to a portion of the closing element made from one component (e.g. linear low density polyethylene (LLDP)) with gaps in places of portions to be formed by the second component (e.g. a thermoplastic elastomer).

In a second step, the second component, e.g. the thermoplastic elastomer, is added to the gaps present in the portion of the closing element made from the first component in the first step. For example, injection molding may be used to add the thermoplastic polymer (or another second component) forming the intended breaking point to the portion of the closing element made from the first component in the first step. Additionally or alternatively, a film made of the thermoplastic polymer (or another second component) may be arranged on a surface area of the closing portion to seal any gaps present e.g. between separate plates forming the closing portion and thereby form the intended breaking point. It is possible to arrange such a film on the side of the closing portion configured to be arranged on an open portion of the fluid line to fluidically close the fluid line and/or on the side of the closing portion facing away from the fluid line if the closing element is arranged on the fluid line.

The fluid line may be any tube or hose suitable for conducting fluid.

The at least one protrusion of the pressure receiving portion projects outwards from the closing portion, the pressure receiving portion or the main body of the closing element. In other words, the protrusion projects away from at least a part of an outer surface of the closing portion, the pressure receiving portion or the main body of the closing element. For example, the protrusion may be regarded as a sub section of the pressure receiving portion that bulges outwards relative from another sub section of the pressure receiving portion. The same may apply if the projection projects outwards from the closing portion or the main body of the closing element.

For example, because the protrusion projects outwards from the closing portion, pressure may be exerted onto the protrusion by a pressure exertion element without the pressure exertion element contacting an outer surface of the closing portion. Thus, it is ensured that the closing portion does never enter and/or completely remains outside of the flow path established upon opening of the closing element.

According to an embodiment of the invention, the pressure receiving portion comprises an annular protrusion running at least along a part of or along the entire length of the outer circumference of the closing element, preferably the main body thereof.

According to another embodiment of the invention, the closing portion comprises at least two plates that are separated from each other by the intended breaking point.

Preferably, the closing portion comprises at least two plates that are connected to each other and/or separated from each other by the intended breaking point and are arranged at an angle to each other.

In an advantageous embodiment, the two plates of the closing portion that are connected to each other and are separated from each other by the intended breaking point and are arranged at an angle to each other to form a roof-like structure with a pointed leading edge.

According to another embodiment of the invention, the pressure receiving portion comprises a plurality of protrusions arranged along the outer circumference of the closing element, preferably at the pressure receiving portion and/or closing portion thereof, wherein the protrusions are preferably separate from another and/or arranged in equal intervals along the outer circumference.

In principle, it would also be possible to arrange the plurality of protrusions along the outer circumference of the main body.

In an advantageous embodiment, the closing portion is formed by a plurality of plates each having the shape of a circle section that are arranged around a center point of the closing portion similar to petals of a flower.

Each plate of the plurality of plates is preferably separated from the adjacent plate by an intended breaking point, e.g. a line of local thinning of the material. In a particularly advantageous embodiment, the closing portion comprises six plates ("petals") and further preferably the main body has a hexagonal base shape.

Preferably, each protrusion of the plurality of protrusions is arranged on a plate forming the closing portion so that pressure applied to each protrusion is selectively transferred to the plate the protrusion is arranged on. The pressure exertion element presses onto the plates, in particular onto the radially outward section of each plate, thus causing each plate to tilt like a lever, so that the radially outward section of each plate and the radially inward section of each plate are moved in opposing directions. The tilting movement of the plates strains the intended breaking point until it breaks. The breaking of the intended breaking point can be further supported by the upper edge of the fluid line closed by the closing element pressing against the plates of the closing portion from the inside of the main body of the closing element. In conjunction with the arrangement of the plates forming the closing portion and the provision of an intended breaking point between each two adjacent plates of the closing portion, the force required to open the closing element can be reduced.

According to another advantageous embodiment, the pressure receiving portion and/or at least one protrusion thereof is present on at least half of the longitudinal length of the closing element in an insertion direction of the fluid line into the closing element.

For example, if the protrusion projects outwards from the main body of the closing element, e.g. in the shape of an annular protrusion, the annular protrusion may be configured so that its length in the longitudinal direction of the closing element (e.g. the insertion direction of the fluid line into the closing element) is at least half of the length of the closing element in this direction.

In other words, the contact surface of the pressure receiving portion that is to be brought into contact with the pressure exertion element may be provided in the distal half of the closing element in an insertion direction of the fluid line into the closing element.

According to another embodiment of the invention, a recess is arranged between the closing portion and the pressure receiving portion and/or the at least one protrusion thereof to allow the closing portion to move upon breaking of the intended breaking point.

The provision of such as recess is especially helpful if the pressure receiving portion and/or at least one protrusion thereof is present on at least half of the longitudinal length of the closing element in an insertion direction of the fluid line into the closing element and the closing portion is formed by two plates arranged at an angle to each other forming a roof-shape. Upon breaking of the intended breaking point, the two plates of the closing portion can move towards a straight or vertical position without this movement being obstructed by the pressure receiving portion and/or at least one protrusion thereof.

According to another embodiment of the invention, the pressure receiving portion comprises a plurality of protrusions arranged at different positions along the longitudinal length of the closing element in an insertion direction of the fluid line into the main body.

For example, the closing portion may comprise at least two plates of different thicknesses that are arranged on the main body of the closing element. Due to the different thicknesses of the plates of the closing portion, the protrusions arranged on the plates are positioned at different positions along the longitudinal length of the closing element in an insertion direction of the fluid line into the main body.

According to another embodiment of the invention, the at least one protrusion of the pressure receiving portion is configured in a hook shape.

Additionally or alternatively, adjacent to the at least one protrusion of the pressure receiving portion a recess is formed.

According to an embodiment of the invention, the pressure receiving portion and/or at least one protrusion thereof at least partially defines a distal end face of the closing element in the insertion direction of the fluid line into the closing element.

This has the advantage that the distance a pressure exertion element to be brought into contact with the pressure receiving portion and/or at least one protrusion thereof by a relative movement of the pressure exertion element and the closing element has to travel before such contact is established is minimized.

Alternatively, the closing element or a connector comprising a fluid line the closing element is arranged on may be moved relative to the pressure exertion element. In this case, the distance the closing element and/or connector has to travel to establish contact to the pressure exertion element is minimized.

According to an embodiment of the invention, the main body has a cylindrical or polygonal, in particular a hexagonal, form.

It has proven especially advantageous if the main body has a polygonal shape and the number of plates forming the closing portion corresponds to the number of edges of the polygonal main body, in particular, wherein the main body has a hexagonal form and the closing portion comprises six plates. This ensures that each plate forming the closing portion can be arranged on a straight edge of the main body which facilitates tilting of the plates, because leverage is optimized.

According to another embodiment of the invention, at a connection point between the closing portion comprising the intended breaking point and the main body of the closing element the material is selectively weakened, preferably by providing at least one recess, to facilitate breaking of the intended breaking point due to pressure being applied to the pressure receiving portion.

For example, the closing portion may comprise a plurality (e.g. six) plates having the shape of circle sections that are arranged around a central point similar to petals of a flower. These plates are preferably connected to a hexagonal main body. At the connection point between the main body and the plates, the material is preferably weakened, e.g. by providing an annular recess running long the outer circumference of the main body.

According to another embodiment, the closing element further comprises a sealing structure at the inner circumference of the main body, preferably in the form of an annular protrusion running along the entire circumference of the main body. Alternatively, the sealing function may be provided by a flush fit between the inner circumference of the main body of the closing element and an outer circumference of a fluid line inserted into the main body.

The sealing structure may be configured to be received in a corresponding annular recess running along the outer circumference of a fluid line to removably hold the closing element to the fluid line.

Furthermore, the closing element may comprise a recess adjacent to the sealing structure arranged in a position radially outwards from the sealing structure to allow radial movement of the sealing structure. This ensures easy mounting of the closing element on a fluid line.

According to an embodiment of the invention, the closing element is at least partially or completely manufactured from polymer material, in particular from linear low density polyethylene and/or high density polyethylene.

The closing element is preferably manufactured by injection moulding.

In an embodiment of the invention, the closing portion comprises six plates arranged like petals of a flower around a central point, wherein each plate has a thickness between 1 mm and 3 mm. The maximum diameter of the closing portion is ca. 16 mm and the main body has a diameter of ca. 10 mm, Another aspect of the invention relates to a connector, preferably a connector of a concentrate container or other disposable, comprising at least one fluid line providing a flow path through the connector via that fluid may be passed into the container to dissolve concentrate and/or fluid may be withdrawn from the container, wherein a closing element according to the present invention is arranged on at least one fluid line of the connector to preferably fluidically close the fluid line.

The at least one fluid line of the connector can comprise only one lumen (only one tube) or can comprise an inner lumen and an outer lumen (a tube in a tube). The outer lumen does not provide a flow path for conducting fluid through the connector but is preferably configured as an annular blind hole.

If the fluid line of the connector comprises only one lumen, the closing element according to the present invention is preferably arranged on this lumen/tube.

If the fluid line of the connector comprises an inner lumen and an outer lumen, the closing element is preferably arranged on an end face of the outer lumen and an end face of the inner lumen is arranged retracted into the outer lumen so that a gap is present between the end face of the inner lumen and the closing element. This ensures that the inner lumen is not brought into contact with the closing element.

The outer lumen preferably does run through the connector to provide a flow path therethrough. Only the inner lumen is used to conduct fluid through the connector and the other lumen serves the purpose of preventing the closing element from coming into contact with the inner lumen.

According to another embodiment of the invention, the connector comprises at least two fluid lines, each fluidically closed by a closing element according to the present invention, wherein the two fluid lines have different lengths, so that a pressure exertion element being moved towards the connector reaches the at least two fluid lines sequentially. Thus, the at least two fluid lines are sequentially opened by the pressure exertion element.

It has proven advantageous in practice if at least one of the fluid lines of the connector comprises a sharp or pointed leading edge pointing away from the connector.

Especially, if a closing element comprising a closing portion formed by two plates arranged slanted to each other to form a roof-shaped closing portion with the intended breaking point connecting the two plates to each other, the sharp or pointed leading edge of the fluid line of the connector corresponds to the adjacent contour of the roof-shaped closing portion, if the fluid line is inserted into the closing element.

Preferably, the leading edge of the at least one of the fluid lines of the connector comprises two slanted sections that are arranged at an angle to each other. Preferably, the angle of inclination of the two slanted sections is equal.

According to an embodiment of the invention, at least one of the fluid lines of the connector comprises an annular recess at its outer circumference to receive a sealing structure of a closing element to thereby hold the closing element to the fluid line.

Another aspect of the present invention relates to a system comprising a closing element according to the present invention, a connector according to the present invention and a pressure exertion element, preferably a connector element of a blood treatment device or a dosing unit thereof, wherein the pressure exertion element is configured to be fluidically connected to the fluid line of the connector by breaking the intended breaking point of the closing element, preferably by a relative movement of the pressure exertion element and the connector.

The pressure exertion element may be moved towards the connector comprising the closing element and/or the connector comprising the closing element may be manually or automatically moved towards the pressure exertion element.

According to an embodiment of the invention, the connector, preferably a connector of a concentrate container, and/or the pressure exertion element, preferably a connector element of a blood treatment device or a dosing unit thereof, comprises at least one fluid line comprising an inner lumen and an outer lumen preferably arranged concentrically to each other.

Preferably, the inner lumen is arranged retracted into the outer lumen. The inner lumen is used to conduct fluid and the closing element is arranged on the outer lumen that does not constitute a flow path through the connector but serves the purpose to ensure that a the closing element is not brought into contact with the inner lumen. Alternatively only one tube and lumen may be present that is used for conducting fluid and is closed by the closing element.

In yet other words, the present invention may be described as follows:

A first aspect of the invention relates to a closing element for a fluid line, preferably a fluid line of a concentrate container, comprising:

- a closing portion configured to be arranged on an end portion of the fluid line to fluidically close the fluid line, wherein the closing portion comprises an intended breaking point, and
- a pressure receiving portion configured to receive pressure applied by a connector element to be fluidically connected to the fluid line by breaking the intended breaking point, wherein
- the pressure receiving portion comprises at least one protrusion projecting outwards from the closing element that is configured to come into contact with the connector element.

The shape and number of the at least one protrusion or protrusions of the pressure receiving portion can be adapted to any specific desired application.

If a container comprising such a closing element is to be connected to a blood treatment device, the connector element of the blood treatment device is moved in such a way as to come into contact with and exert pressure on the pressure receiving portion of the closing element. In this case the connector element of the blood treatment device functions as a pressure exertion element. The connector element may be moved towards the connector of the container and thus the fluid line closed by the closing element by linear movement or a tilting movement, e.g. if the connector element of the blood treatment device is arranged on a movable flap of the blood treatment device. For example, the connector element may have an outer lumen that receives the closing element and abuts/contacts the pressure receiving portion thereof. Alternatively, the connector bearing the closing element may be moved towards the connector element of the blood treatment device.

The closing element, that preferably has the shape of a cap, is pressed down onto the fluid line until the intended breaking point of the closing portion breaks and the fluid line is fluidically opened.

According to an aspect of the invention, the pressure receiving portion comprises an annular protrusion running at least along a part of or along the entire length of the outer circumference of the closing element, in particular of the main body or closing portion or pressure receiving portion thereof.

Alternatively or additionally, the pressure receiving portion can comprise a plurality of protrusions arranged along the outer circumference of the closing element, wherein the protrusions are preferably separate from another and/or arranged in equal or different intervals along the outer circumference.

Providing separate protrusions ensures efficient force transfer from the pressure receiving portion to the intended breaking point, especially if the closing portion comprises several plates arranged around a central point like petals of a flower and an intended breaking point, e.g. a line of thinner material is present between each two plates or petals.

In order to reduce the amount of space required to open the fluid line covered by the closing element by a connector element of a blood treatment device, it has proven advantageous in practice, if the pressure receiving portion and/or at least one protrusion thereof is present on at least half of the longitudinal length of the closing element in an insertion direction of the fluid line into the closing element. In other words the surface for establishing contact between the closing element and the pressure exertion element (or connector element) is moved into the proximal half of the closing element in the direction of the movement of the pressure exertion element towards the closing element.

In other words, if the closing element is arranged on the end side of the fluid line like a cap, the protrusion of the pressure receiving portion is not only present at a lower end of the closing element (distal to the end face of the fluid line). Instead, the protrusion extends along the body of the closing element in the longitudinal direction of the closing element (insertion direction of the fluid line) at least half way up towards the upper end of the closing element (covering the end face of the fluid line). This is especially advantageous if the closing portion comprises two plates arranged at an angle to each other to form a roof-shape and connected to each other via a central intended breaking point.

This has the advantage that if the connector element of the blood treatment device is moved downwards onto the closing element to contact the pressure receiving portion and press the closing element down onto the fluid line until the intended breaking point opens, the connector element of the blood treatment device has to be moved a shorter distance before it abuts the pressure receiving portion. Thus, less space is required for the components for fluidically coupling the concentrate container to the blood treatment device or dosing unit allowing a more compact design of the dosing unit.

In order to minimize the distance the connector element of the blood treatment device has to travel to establish contact with the pressure receiving portion, the pressure receiving portion and/or at least one protrusion thereof can be arranged to define a distal end face of the closing element in the insertion direction of the fluid line into the closing element. In other words, the plane of the upper end face of the closing element or cap may be at least partially be defined by the pressure receiving portion when the closing element is arranged on a fluid line to fluidically close that fluid line.

It has further proven advantageous in practice, if the pressure receiving portion comprises a plurality of protrusions arranged at different positions along the longitudinal length of the closing element in an insertion direction of the fluid line into the closing element. In this case, if the connector element of the blood treatment device is moved down onto the closing element, the protrusions arranged at different longitudinal positions are sequentially opened (starting with the top protrusion) as the connector element moves from the upper end of the closing element to the lower end of the closing element. For example, in the case of the closing portion comprising several plates arranged like petals of a flower separated from each other via intended breaking points, one plate or multiple plates can have different thicknesses, so that the pressure exertion element sequentially abuts the plates of different thicknesses. The thickness of the plates can be varied depending on the specific application, for example, only one of the plates of the closing portion can have a thickness that differs from the thickness of the other plates that have a uniform thickness. Alternatively, two or more plates may have differing thicknesses from the rest of the plates. Thus, the flow diameter of the opening of the concentrate container can be sequentially increased in a step-wise fashion and the maximal force required for opening the closing element can be reduced.

According to advantageous embodiments of the invention, the closing element comprises a cylindrical or hexagonal main body for receiving an end portion of the fluid line. Other geometries of the main body, e.g. a heptagonal, triangular or quadratic base area, are possible, preferably as long as the closing element can still be arranged on a fluid line to be closed in the fashion of a cap.

If a hexagonal main body is used in conjunction with a closing portion comprising six plates, this offers the advantage that each of the six plates of the closing portion can be arranged on a straight edge of the hexagonal main body. This facilitates opening of the closing element upon the exertion of pressure on to the pressure receiving portion due to the straight edges supporting the tilting motion of the plates of the closing portion. The plates of the closing portion act as levers that break the intended breaking point. The configuration of the intended breaking point as straight lines arranged between the plates optimizes leverage.

The closing element preferably having the form of a cap can comprise a main body configured to receive the fluid line to be closed and a closing portion configured to fluidically close the fluid line.

To facilitate a breaking of the intended breaking point by the connector element and thus ensure an easy and reliable opening of the container, at least one connection point between the closing portion comprising the intended breaking point and the main body of the closing element the material can be selectively weakened, preferably by providing at least one recess.

In this embodiment, preferably the closing portion and the pressure receiving portion are integrally formed so that upon the exertion of pressure onto the pressure receiving portion the closing portion or at least a part thereof is moved by a tilting motion to break the intended breaking point.

The weakening of the material at the at least one connection point between the closing portion comprising the intended breaking point and/or the pressure receiving portion and the main body of the closing element allows the closing portion and/or the pressure receiving portion to easily tilt and thereby break the intended breaking point. This is especially relevant in the case of the closing portion comprising multiple plates arranged like petals of a flower around a central point, wherein the plates are separated from each other by lines of weakened material forming intended breaking points.

To improve the storage ability of a container closed by a closing element according to the present invention, the closing element may further comprise a sealing structure at the inner circumference of the main body, preferably in the form of an annular protrusion running along the entire circumference of the main body, to ensure an air-tight sealing of the container.

Preferably, the closing element is at least partially or completely manufactured from polymer material, in particular from linear low density polyethylene and/or high density polyethylene. These materials offer an optimal tradeoff between mechanical stability rigidity and thus reliable breaking of the intended breaking point and compliance ensuring the effort required for breaking the closing element remains reasonable. Elastomers are also possible, either alone or in combination with linear low density polyethylene and/or high density polyethylene.

Another aspect of the invention relates to a connector, preferably a connector of a concentrate container or other disposable, wherein a closing element according to the present invention is fixedly or removably arranged on at least one fluid line of the connector to preferably fluidically close the fluid line.

The fluid line preferably provides a flow path through the connector and can e.g. be used to conduct fluid into the concentrate container or to withdraw liquid concentrate from the container. The fluid line can be any tube or hose.

The connector of the disposable can comprise at least one holding element, e.g. in the shape of a hook configured to hold the connector in the vicinity of a connector element of a blood treatment device or dosing until thereof to that the connector of the disposable shall be connected.

The connector of the disposable may also comprise a structure for opening a valve of the connector element of the blood treatment machine or dosing unit thereof upon connection of the connector of the disposable to the connector element of blood treatment machine or dosing unit thereof. For example, a fluid line of the connector of the disposable may comprise a central pole or spike configured to remove a valve element of its valve seat in a valve of the blood treatment machine or dosing unit thereof to thereby enable fluid flow through the valve. The shape of the pole or spike is arbitrary, any structure suitable for opening the valve upon connector of the connector to the connector element may be chosen.

Preferably, the fluid line of the connector comprises an inner lumen or inner tube and an outer lumen or outer tube, wherein the closing element is arranged on an end face of the outer lumen and an end face of the inner lumen is arranged retracted into the outer lumen so that a gap is present between the end face of the inner lumen and the closing element. In other words, the outer tube serves to protect or shield the inner lumen from contact with the closing element. This offers the advantageous that contamination of the inner tube that is used to conduct fluid is minimized.

According to an advantageous embodiment, the connector comprises at least two fluid lines, each fluidically closed by a closing element according to the present invention, wherein the two fluid lines project different lengths from an end face of the connector.

If a concentrate container comprising such a connector is to connected to a blood treatment device or dosing unit, the two fluid lines are sequentially opened and connected to the blood treatment device or dosing unit, because first, the fluid line projecting further from the connector towards the blood treatment device or dosing unit is opened and secondly the shorter fluid line is opened and connected.

Yet another aspect of the invention relates to a system comprising a closing element according to the present invention, a connector (preferably of a concentrate container) according to the present invention and at least one connector element, preferably a connector element of a blood treatment device or a dosing unit thereof, wherein the connector element is configured to be fluidically connected to at least one fluid line of the connector by breaking the intended breaking point of the closing element arranged thereon.

In such a system, it has proven advantageous, if the connector, preferably connector element of a blood treatment device or a dosing unit thereof, comprises an inner lumen and an outer lumen preferably arranged concentrically to each other. In each case, the inner lumen or tube and the outer lumen or tube can form a fluid line.

The connector element of the blood treatment machine or dosing unit thereof may be moved towards and/or onto the connector of the disposable and its fluid lines by a translational or linear movement, or by a rotational movement in that for example, the connector element is arranged in a flap of the blood treatment device that is tilted to come into contact with the connector of the disposable.

It has proven advantageous if the connector element of the blood treatment machine is configured movable relatively to a main body of the blood treatment device, so that it can be selectively moved to establish a connection to the disposable.

For example, the connector element of the blood treatment device or dosing unit may comprise a portion that is movable relative to the main body of the device for establishing a fluid connection between the disposable and the blood treatment device and another portion, that may be fixedly arranged at the main body of the device, for holding the connector of the disposable in place.

Preferably, the movable portion contains the fluid lines of the blood treatment device and/or is arranged further up on the main body of the blood treatment device, if the blood treatment device is placed onto a horizontal plane in its normal operation position. The movable portion containing the fluid lines can be moved towards the connector by a translational or rotational movement.

Further features, effects and advantages of the present invention become apparent from the subsequent detailed description of embodiments of the invention under reference to the appended drawings. The same or similar components are indicated by the same reference signs. In the drawings.

Figure 3A:
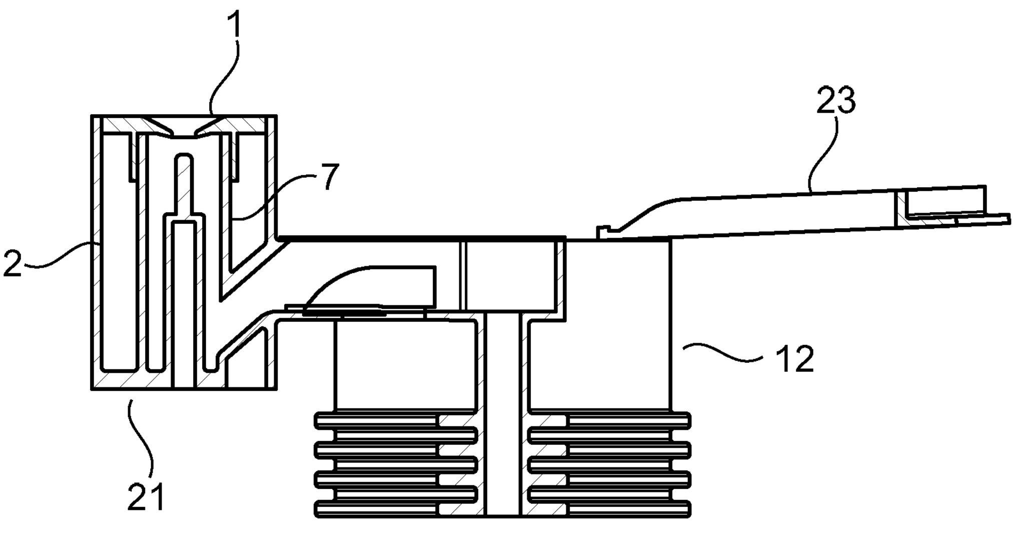
Figure 3B:
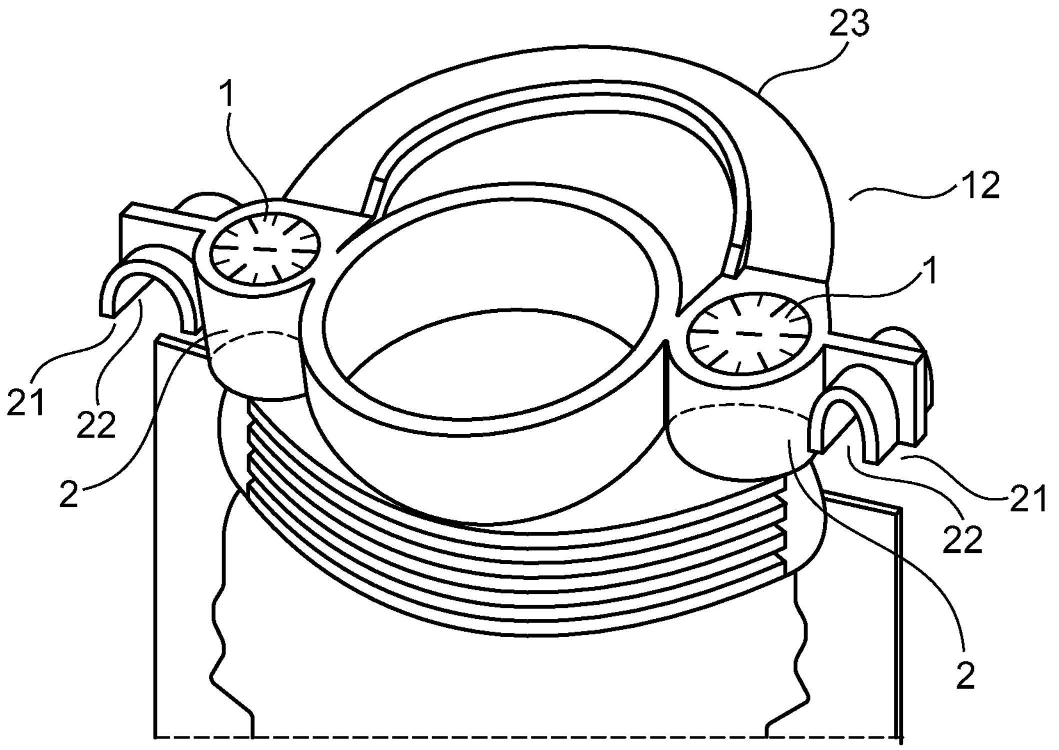
Figure 4:
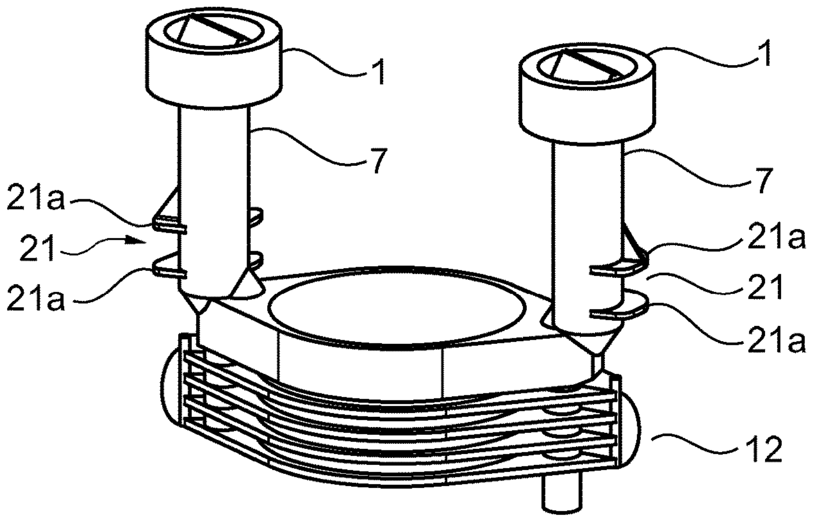
Figure 5:
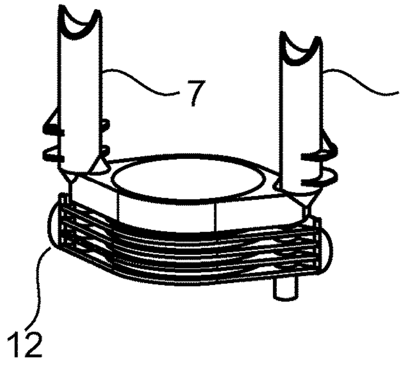
Figure 6:
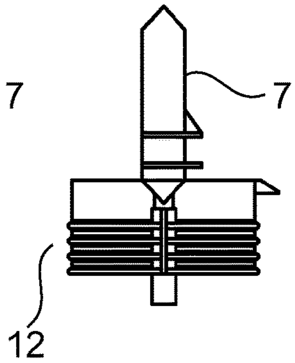
Figure 7:
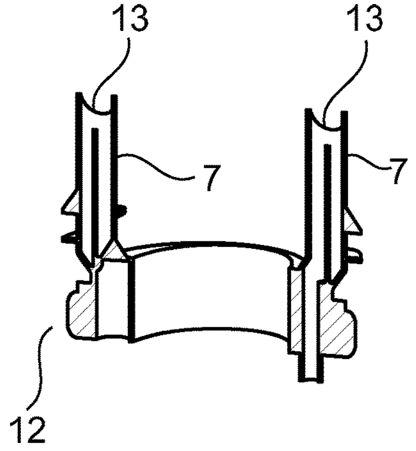

FIG. 3*a* shows a connector of a concentrate bag according to the invention;

FIG. 3*b* shows another connector of a concentrate bag according to the invention;

FIG. 4 shows a connector of a concentrate bag according to the invention comprising two fluid lines each closed by a closing element according to a second embodiment of the invention;

FIG. 5 shows a perspective view of the connector of FIG. 4;

FIG. 6 shows a side view of the connector of FIG. 4;

FIG. 7 shows a sectional view of the connector of FIG. 4

Figure 8:
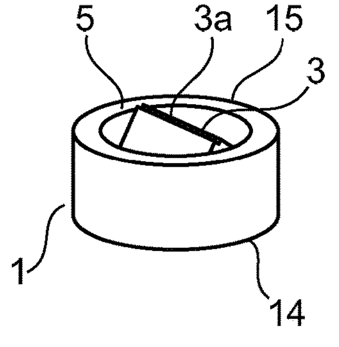
Figure 9:
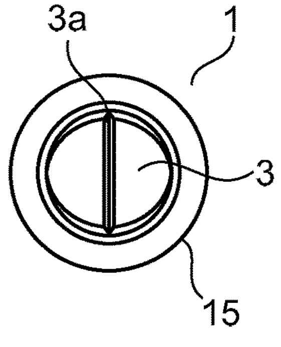
Figure 10:
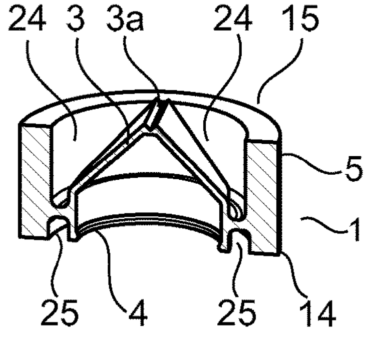
Figure 17:
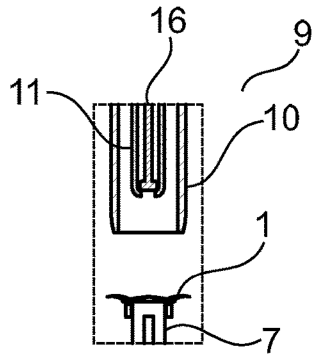
Figure 18:
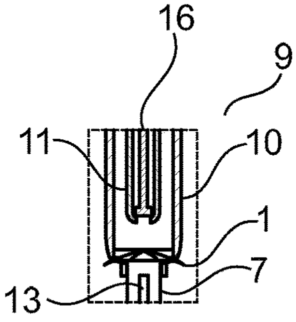
Figure 19:
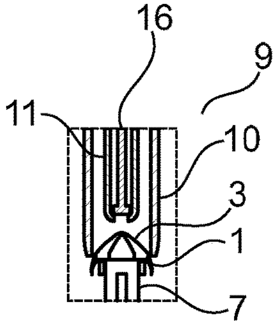
Figure 20:
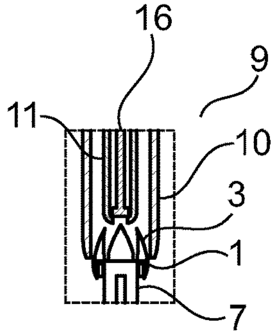
Figure 21:
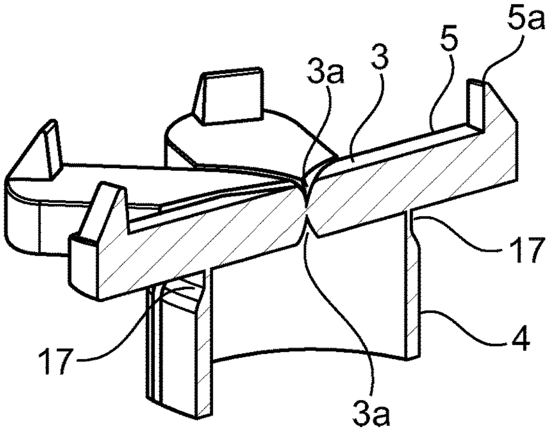
Figure 22:
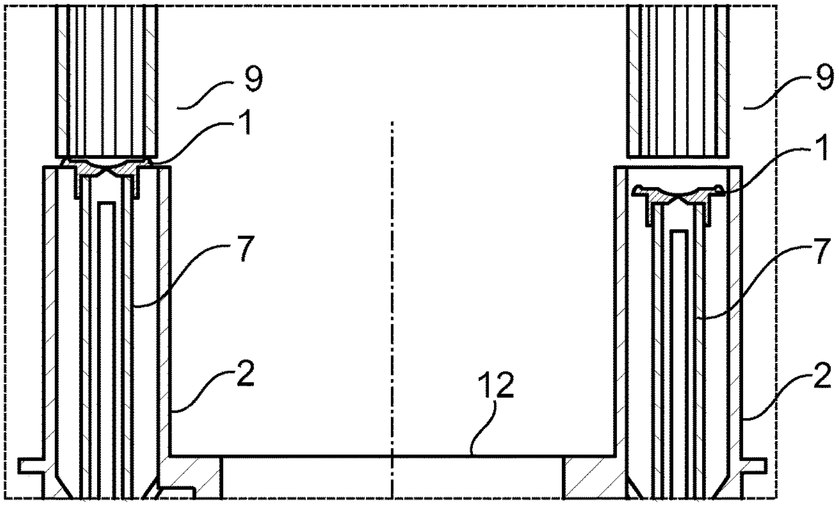
Figure 23:
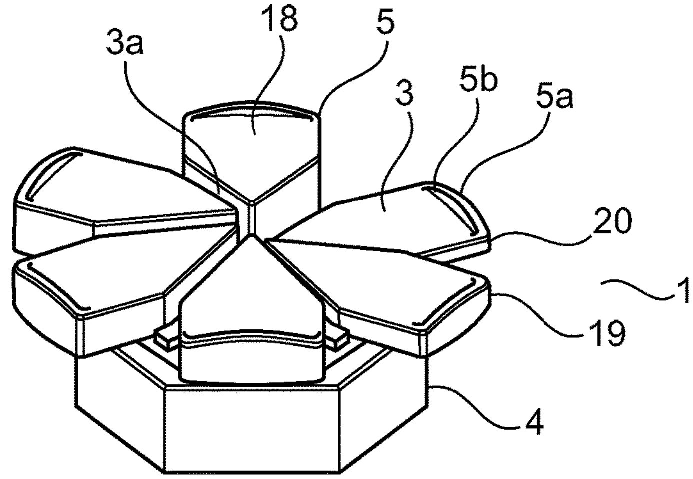

FIG. 8 shows a perspective view of a closing element according to the second embodiment;

FIG. 9 shows a top view of the closing element of FIG. 8;

FIG. 10 shows a sectional view of the closing element of FIG. 8;

FIG. 11 shows a sectional view of the closing element of FIG. 8 arranged on the fluid line of a connector of FIG. 4;

FIG. 12 shows a first step in the connection process of the connector and closing element of FIG. 11 being connected to a connector element of a blood treatment device;

FIG. 13 shows a second step in the connection process of the connector and closing element of FIG. 11 being connected to a connector element of a blood treatment device;

FIG. 14 shows a third step in the connection process of the connector and closing element of FIG. 11 being connected to a connector element of a blood treatment device;

FIG. 15 shows a perspective view of a closing element according to a third embodiment;

FIG. 16 shows a sectional view of the closing element of FIG. 15;

FIG. 17 shows a first step in the connection process of a connector and closing element of FIG. 15 being connected to a connector element of a blood treatment device;

FIG. 18 shows a second step in the connection process of a connector and closing element of FIG. 15 being connected to a connector element of a blood treatment device;

FIG. 19 shows a third step in the connection process of a connector and closing element of FIG. 15 being connected to a connector element of a blood treatment device;

FIG. 20 shows a fourth step in the connection process of a connector and closing element of FIG. 15 being connected to a connector element of a blood treatment device;

FIG. 21 shows sectional view of a closing element according to another embodiment;

FIG. 22 illustrates the sequential opening of two fluid lines each closed by a closing element according to the present invention;

FIG. 23 shows sectional view of a closing element according to yet another embodiment.

Figure 24A:
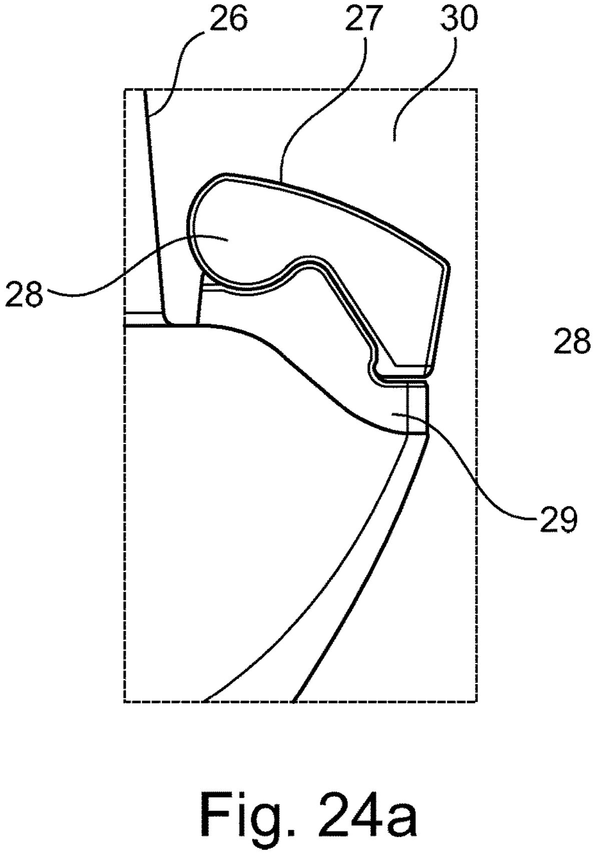
Figure 24B:
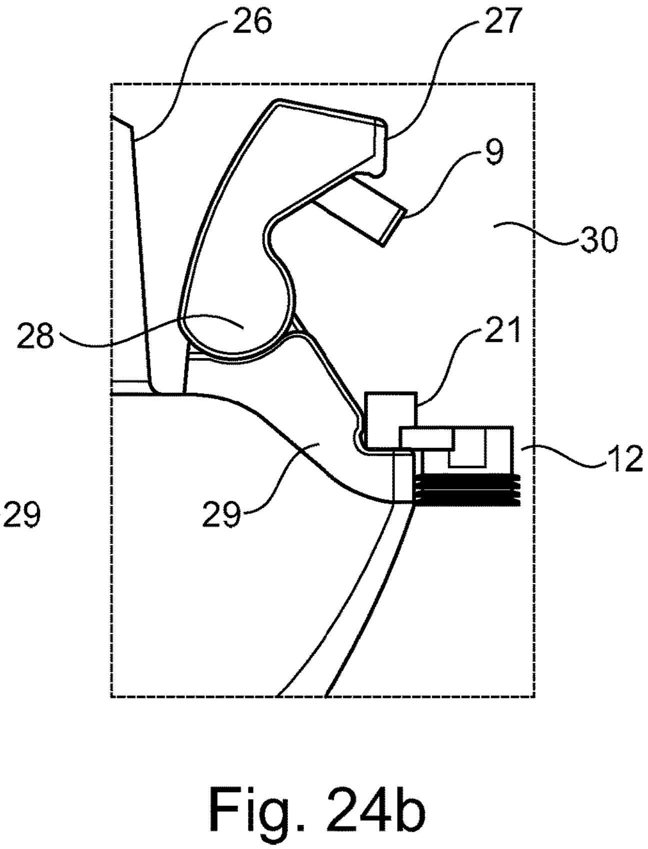
Figure 25:
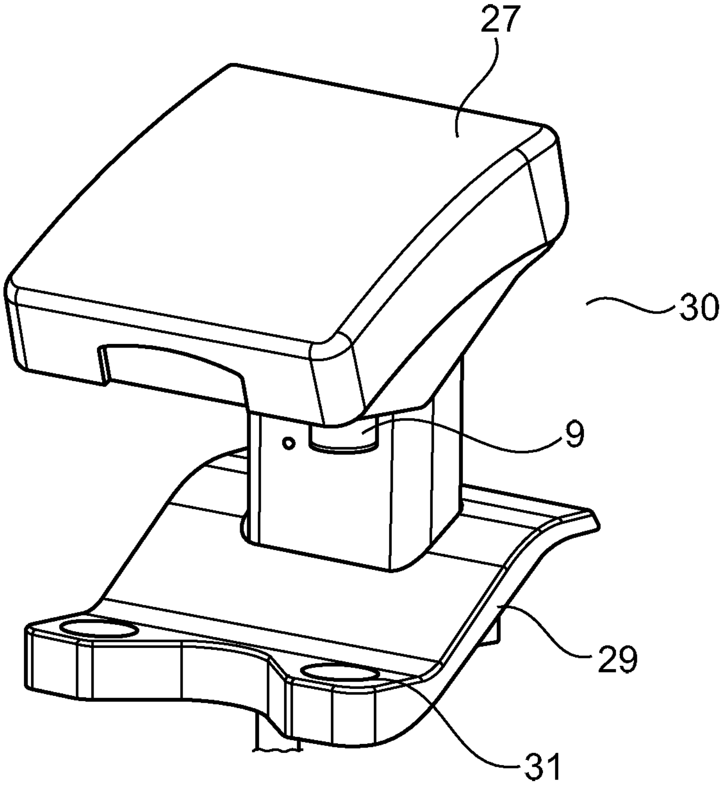
Figure 26:
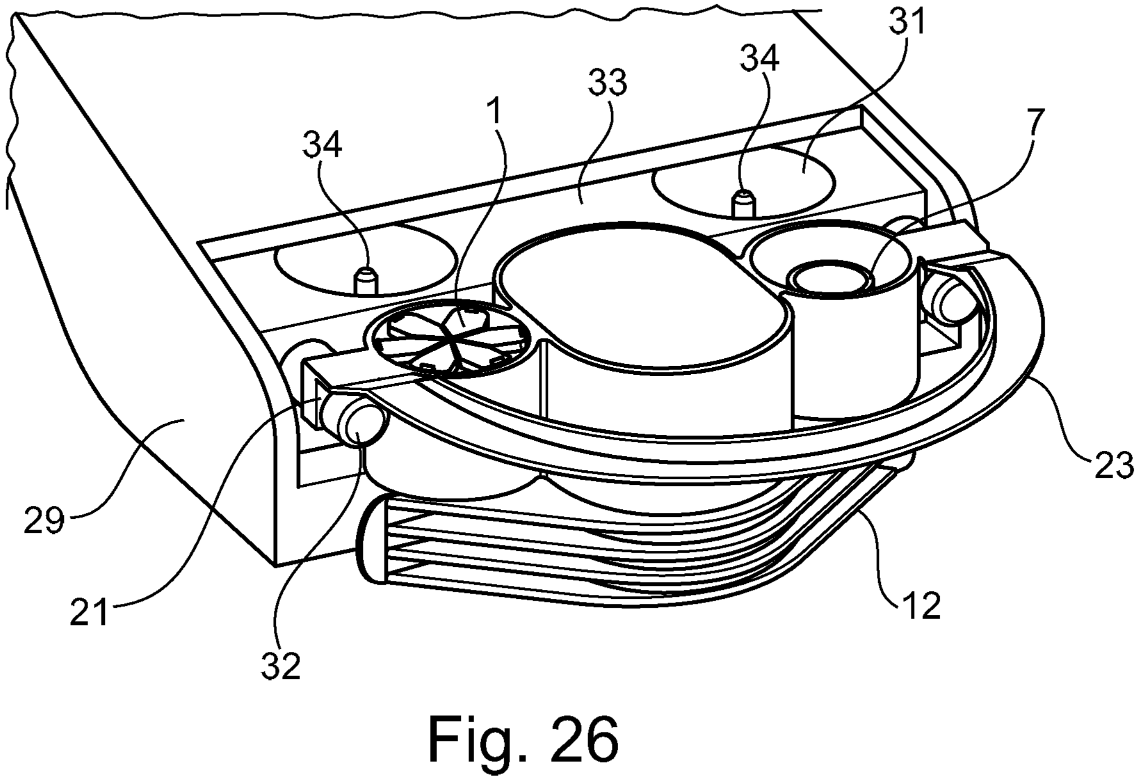

FIG. 24*a* shows a machine connector of a blood treatment machine that is movable by rotation in a closed state;

FIG. 24*b* shows the machine connector of FIG. 24*a* in an open state;

FIG. 25 shows a different machine connector of a blood treatment machine that is translationally movable;

FIG. 26 shows a connector of a concentrate container attached to a blood treatment device.

Figure 1:
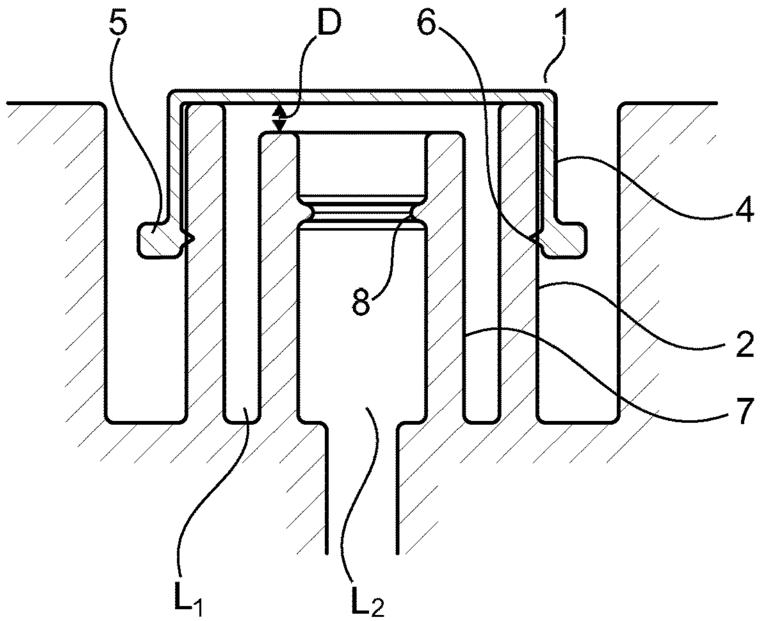
FIG. 1 shows a cross section of a fluid line closed by a closing element according to a first embodiment the present invention.

As shown in FIG. 1, a closing element 1 according to a first embodiment the present invention is arranged in the fashion of a cap on the end of a fluid line 1 that preferably is part of a connector of a container for concentrate. The closing element 1 has a closing portion 3 fluidically closing the fluid line, in particular the outer tube 2 thereof, a cylindrical main body 4 and a pressure receiving portion 5 that in this embodiment is configured as an annular protrusion extending along the outer circumference of the main body 4 at the lower end of the closing element 1.

On the inner circumference of the main body 4, the closing element 1 comprises an annular sealing protrusion 6 that seals the gap between the inner circumference of the main body 4 and the outer tube of the outer tube 2 of the fluid line. The fluid line also comprises an inner tube 7 that is arranged concentrically to the outer tube and ends short of the end face defined by the outer tube 2 so that the inner tube 7 is arranged retracted into the lumen of the outer tube 2, so that a gap or distance D is ensured between the end face of the inner tube 7 and the closing element 1.

The fluid line has an outer lumen L1 and an inner lumen L2. The inner lumen L2 is used to conduct fluid. The inner circumference of the inner lumen L2 comprises an annular sealing protrusion 8. The outer lumen L1 is not used to conduct fluid but serves the purpose of ensuring a distance between the sterile inner lumen L2 and the closing element 1. The outer lumen can be regarded as an annular blind hole that does not penetrate the connector 12.

Figure 2:
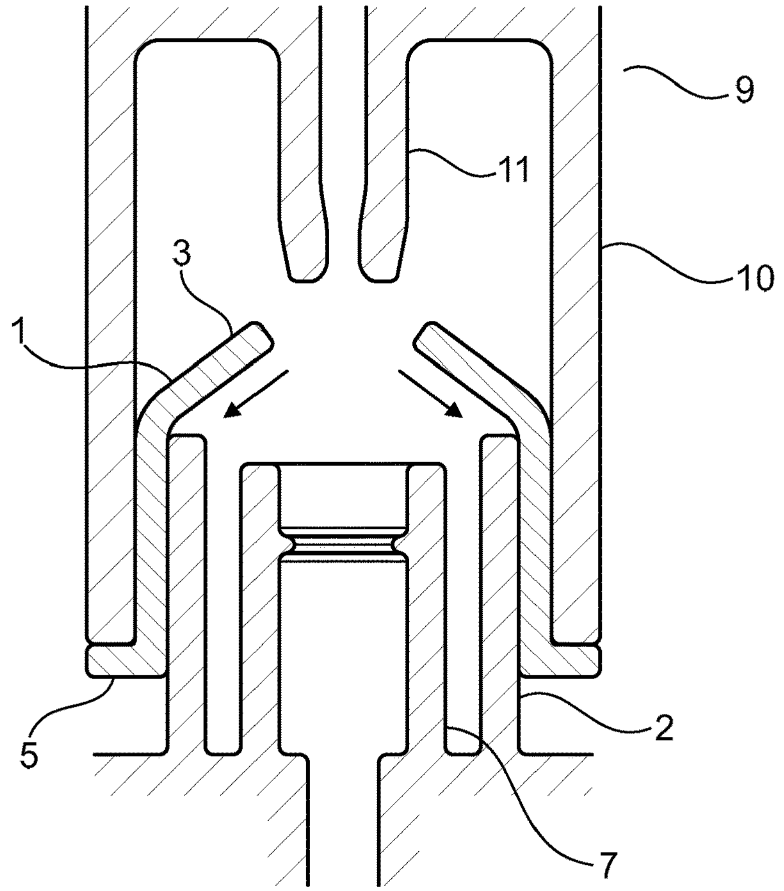
FIG. 2 shows the cross section of a fluid line closed by a closing element according to the first embodiment the present invention as shown in FIG. 1, wherein the intended breaking point of the closing element is broken.

FIG. 2 shows the cross section of a fluid line closed by a closing element 1 as shown in FIG. 1, wherein the intended breaking point of the closing element 1 is broken by a connector element 9 being moved downwards onto the fluid line of the concentrate bag. In principle, it is also possible to move the connector of the concentrate bag up towards the connector element 9 to thereby rupture the closing element 1.

The connector element 9 is part of a blood treatment device or dosing unit thereof and comprises an outer tube 10 configured to press onto the pressure receiving portion 5 of the closing element 1 to open the closing element 1 at the intended breaking point as indicated by the arrows in FIG. 2. The connector element 9 further comprises an inner tube 11 configured to be inserted into the inner tube 7 of the connector to establish a fluid connection between the concentrate container and the blood treatment device. Via this fluid connection, fluid may be pumped into the concentrate container or withdrawn thereof.

FIG. 3*a* shows a connector 12 of a concentrate bag according to the present invention. The connector 12 is made in one piece out of a polymer material. The connector 12 comprises two attachments elements 21 for attaching the connector 12 to a blood treatment device. In this embodiment, the attachment elements 21 have the shape of hooks configured to be inserted into corresponding recesses (e.g. rinsing recesses) of the connector element of the blood treatment device.

Generally, the connector element of a blood treatment device comprises two parts: a first part comprises at least one fluid line and is used to establish a fluid connection to e.g. a concentrate container. The second part comprises at least one recess, usually two recesses, configured to receive the at least one fluid line of the first part to short-circuit the fluid line during rinsing of the machine. In the present case, the attachment elements 21 or hooks of the connector 12 are configured to be inserted into these rinsing recesses to affix the connector and thus the concentrate container to the blood treatment device. The connector 12 comprises a handle 23 for moving the concentrate bag attached thereto.

After the connector 12 has been thus affixed to the blood treatment device, the connector element of the blood treatment device, in particular the first part thereof bearing the fluid lines, is moved relative to the connector 12 to press onto the closing element 1 arranged on the open end of the tube 7 of the connector 12 that provides a flow path through the connector and into the concentrate container. The connector element of the blood treatment device exerts pressure onto the closing element 1 until the intended breaking point thereof breaks and the closing element 1 is opened. The outer tube 2 does not serve the purpose of conducting fluid but ensures a good fit of the attachment element 21 in the rinsing recess of the blood treatment device.

FIG. 3*b* shows a different embodiment of a connector 12 according to the present invention. In this embodiment, the attachment elements 21 have a different shape and are configured as curved arms reaching out from the body of the connector 12. These arms define a u-shaped groove 22 configured to receive a corresponding attachment element of the blood treatment device that can have e.g. a bar-like or pole-like shape.

In FIG. 3*b* it can be seen that the connector 12 comprises two fluid lines that are each closed by a closing element 1.

FIG. 4 shows a connector 12 of a concentrate bag according to another embodiment of the invention comprising two fluid lines each having only one tube 7 that is used for conducting fluid each closed by a closing element 1 according to a second embodiment of the invention. The tube 7 comprises a lumen for conducting fluid.

The connector 12 shown in FIG. 4 comprises two attachment elements 21 each arranged on one of the tubes 7. The attachment elements 21 each comprise two parallel protrusions projecting from the outer circumference of each tube 7 outwards in radial direction and are arranged at different positions along the longitudinal axis of each tube 7. The attachment elements 21 are configured to receive a corresponding attachment element of the blood treatment device that can have e.g. a bar-like or pole-like shape.

As shown in FIG. 5 the end faces of the tube 7 of each fluid line of the connector 12 are slanted in two directions. This ensures that locally at the tip of the tube 7 a larger pressure may be exerted than in a case in that a horizontal end face is used. It is also possible to have end faces slanted in only one direction or having a horizontal end face. However, providing end faces slated in two directions and arranged at an angle to each other has the advantageous effect that the distance that needs to be travelled by the pressure exertion element (e.g. a connector element of a blood treatment device) or the connector can be reduced thus allowing for a more compact design of the pressure exertion element, in particular a connector element of a blood treatment device. The geometries of the end faces are variable and can be adapted to any desired application. FIG. 6 shows a side view of the connector 12 of FIGS. 4 and 5.

As shown in FIG. 7, one or both or more or all of the fluid lines of the connector 12 can be equipped with a central pole configured to open a valve in the connector element of a blood treatment device or dosing unit upon connection of the connector 12 thereto by removing a valve element from a corresponding valve seat to open the valve and enable fluid flow therethrough.

FIG. 8 shows a perspective view of a closing element 1 according to the second embodiment. In this embodiment, the pressure receiving portion 5 is not only present at the lower end of the closing element 1 as shown in FIG. 1 but extends all the way up from a lower end face 14 of the closing element to an upper end face 15. In this embodiment, the pressure receiving portion 5 defines the plane of the upper end face 15. This embodiment offers the advantage that a connector 9 only has to be moved a short distance before its outer tube 10 abuts the pressure receiving portion 5 and can exert pressure to open the closing element 1.

FIG. 9 shows a top view of the closing element 1 of FIG. 8. In this view, the intended breaking point 3*a* of the closing portion 3 is clearly visible. The closing portion is formed of two slanted surfaces leaning against each other in the fashion of a roof. The cylindrical main body 4 of the closing element is visible between the closing portion 3 and the pressure receiving portion 5.

FIG. 10 shows a sectional view of the closing element of FIG. 8. The cylindrical main body 4 of the closing element is visible between the closing portion 3 and the pressure receiving portion 5 and the intended breaking point 3*a* is easily seen.

The contour of the closing portion 3 has a roof-shape and follows the contour of the leading edge of the tube 7 of the connector 12.

FIG. 11 shows a sectional view of the closing element 1 of FIG. 8 arranged on the tube 7 of a fluid line of the connector 12. The sealing structure 6 present on the inner circumference of the main body 4 of the closing element 1 is received in a corresponding annular recess in the outer circumference of the tube 7 to removably lock the closing element 1 to the tube 7 via a form-fit mechanism.

A recess 24 is present between the closing portion 3 and the pressure receiving portion 5. This recess 24 allows the two angular plates of the closing portion 3 to move towards a straight position upon breaking of the intended breaking point 3*a*.

Another recess 25 is present in a radially outward position from the sealing structure 6 to allow the sealing structure 6 to flexibly move upon insertion of a fluid line, e.g. the tube 7, into the closing element 1.

FIG. 12 shows a first step in the connection process of the connector 12 and closing element 1 of FIG. 11 being connected to a connector element 9 of a blood treatment device. In this step, the connector element 9 and the tube 7 are aligned and brought into proximity to each other. The connector 12 is attached to the connector element of the blood treatment device via the attachment elements 21 comprising the protrusions 21*a*.

FIG. 13 shows a second step in the connection process of the connector 12 and closing element 1 of FIG. 11 being connected to a connector element 9 of a blood treatment device. At this stage, the connector 9 has been moved downwards towards the connector 12 until the outer tube 10 of the connector 9 presses onto the pressure receiving portion 5 of the closing element 1 and moves the closing element 1 downwards along the longitudinal direction of the tube 7, until the closing element is opened as shown in FIG. 13.

As shown in FIG. 14, in a third step the connector element 9 is moved further downward until the central pole 13 of the tube 7 enters an inner lumen of the inner tube 11 of the connector and thereby removes the valve element 16 from its valve seat to enable fluid flow through the lumen of the inner tube 11 into the concentrate container.

FIG. 15 shows a perspective view of a closing element 1 according to a third embodiment. The closing element comprises a main body 4 and in this embodiment six elements or plates movably joined to the main body 4 that together form the closing portion 3 and the pressure receiving portion 5 of the closing element. These elements are arranged in the fashion of flower petals. Each plate has the shape of a section of a circle. The outer edges of each plate in the radial direction are arranged in a rectangular shape.

At its outer edge, each of these petals is equipped with a protrusion 5*a* that is part of the pressure receiving portion 5 and may be configured as a hook to hold e.g. an outer tube 10 of a connector element 9 of a blood treatment device. Each plate or petal, in particular the pressure receiving portion thereof, projects outwards over the main body 4 of the closing element 1, so that upon the exertion of pressure thereon, each plate can easily tilt. The plates thus act as levers.

The elements forming the petals of the flower-shape are separated from each other by intended breaking points 3*a*. In conjunction with the design of the intended breaking point and the shape of the plates, the provision of separate protrusions has the advantageous effect that the force and strain acting on the intended breaking points upon the exertion of pressure on the plates is optimized.

FIG. 16 shows a sectional view of the closing element of FIG. 15.

FIG. 17 shows a first step in the connection process of a tube 7 closed by a closing element 1 of FIG. 15 being connected to a connector element 9 of a blood treatment device. At the stage shown in FIG. 17, the connector element 9 and the tube 7 comprising the closing element 1 are aligned to each other.

At the stage shown in FIG. 18, the connector element 9 has been moved towards the closing element 1 so that the leading edge of the outer tube 10 abuts the pressure receiving portion 5 of the closing element 1.

At the stage shown in FIG. 19, the connector element 9 has been moved further onto the tube 7 and presses onto the pressure receiving portion 5 of the closing element 1 so that the closing portion 3 of the closing element and thus the intended breaking point 3*a* thereof is strained due to the tilting or rotating movement of the elements ("petals") forming the closing portion 3. The edge of the tube 7 presses against the elements forming the closing portion from the inside of the closing element 1 to facilitate the opening thereof.

At the stage shown in FIG. 20, the connector element 9 has been moved so far onto the tube 7 that the pressure applied on the pressure receiving portion 5 of the closing element 1 exceeds the force required to break the intended breaking point 3*a* that is broken in FIG. 20. As shown in FIG. 20, the elements ("petals") forming the closing portion 3 have tilted or rotated to thereby open the closing element 1.

Thus, in this embodiment, the closing element 1 is opened by a tilting or rotating movement of the elements of the closing portion that act as levers.

FIG. 21 shows sectional view of a closing element 1 according to another embodiment. In this embodiment, the material at a connection point 17 between the elements ("petals") forming the closing portion 3 and pressure receiving portion 5 and the main body 4 of the closing element 1 has been selectively weakened to ensure easy tilting/rotating of the elements ("petals") forming the closing portion 3 and pressure receiving portion 5 upon the application of pressure thereon.

The weakening of the material preferably involves the removal of up to 50% of the material, preferably up to 30% or up to 20% of the material. Depending on the material, a removal of up to 80% of the material can be possible.

FIG. 22 illustrates the sequential opening of two fluid lines, in this case the inner tubes 7 thereof, each closed by a closing element 1 according to the present invention. The inner tube 7 arranged to the left in FIG. 22 projects further away from the connector 12 and thus is closer to the connector element 9 of the blood treatment device. As the connector element 9 of the blood treatment device is moved towards the connector 12, the tube 2 on the left is reached by the connector element 9 first and thus is also opened first.

FIG. 23 shows sectional view of a closing element 1 according to yet another embodiment. In this embodiment, the main body 4 of the closing element 1 has a hexagonal shape. The closing portion 3 and the pressure receiving portion 5 are formed by six elements arranged like the petals of a flower.

In this embodiment, each protrusion 5*a* of the pressure receiving portion 5 of each petal is formed by a grove or recess 5*b*. The protrusion 5*a* protrudes relative to the surface defined by the grove 5*a*.

As illustrated in FIG. 23, the protrusions 5*a* of the pressure receiving portion 5 and/or the elements forming the closing portion 3 and/or the pressure receiving portion 5 may be arranged at different positions along the longitudinal direction of the closing element 1.

For example, in FIG. 23 the element arranged top most in the longitudinal direction is indicated by reference numeral 18. One of the four elements arranged second from the top in the longitudinal direction is indicated by reference numeral 19. The element indicated by reference numeral 20 is arranged lowest in the longitudinal direction of the closing element 1. Thus, the element 18 has a larger thickness than the elements 19 and the element 20 has the smallest thickness. All elements 18, 19, 20 forming the closing portion 3 are attached to the hexagonal main body 4 in the same longitudinal position, e.g. on a common continuous edge of the hexagonal main body. The elements are plates in this embodiment.

Thus, if a connector element 9 of a blood treatment device is moved onto the closing element 1 coming from the top in FIG. 23, the leading edge of the outer tube 10 of the connector element 9 first hits the top most element 18, then hits the intermediate elements 19 and finally hits the lowest element 20. Thus, the flow cross section of the closing element is sequentially enlarged in a step-wise fashion. In addition to that, the force required for opening the closing element can be reduced.

FIG. 24*a* shows a machine connector 30 of a blood treatment device 26 comprising a first part 27 that is movable by rotation around a hinge 28 and a second part 29. In the state shown in FIG. 24*a*, the connector element 26 is closed so that the first part 27 abuts the second part 29 that is unmovably affixed at the blood treatment device 26.

The first part 27 comprises two connector elements 9 in the shape of fluid lines for fluidically connecting the blood treatment device 26 e.g. to a concentrate container. The connector elements 9 can have the configuration shown in FIGS. 1,2 and 17-20. The first part 27 can have the shape of a cap or flap that can be moved via the hinge 28. The movement of the first part 27 can be achieved manually or automatically via a motor. The movement of the first part 27 opens the closing element(s) 1 present on the connector 12 and establishes a fluid connection between the blood treatment device 26 and the connector 12.

FIG. 24*b* shows the machine connector 30 of FIG. 24*a* in an open state. A connector 12 has been affixed to the second part 29. The second part 29 comprises two recesses (not visible in FIG. 24*b*) into that the two attachment elements 21 of the connector 12 have been inserted. The first part 27 comprises two connector elements 9, i.e. fluid lines, that each can be inserted into a recess of the second part 29 for rinsing or can be used to establish a fluid connection to a concentrate container via the connector 12.

The connector elements 9/fluid lines of the first part of the machine connector 30 of the blood treatment device 26 preferably each comprise an inner tube 11 and an outer tube 10 and thus contain two lumina. The inner tube 11 serves the purpose of conducting fluid and is arranged retracted within the outer tube 10. The outer tube 10 is used e.g. for exerting pressure onto a closing element 1. After the closing element 1 has been opened by the outer tube 10, the inner tube 11 is inserted into the fluid line (e.g. the tube 7) of the connector 12 to fludicially connect the blood treatment device 26 and the connector 12 and the concentrate container attached thereto. Thus, the sterile inner tube 11 is never brought into contact with the non-sterile closing element 1.

In the lumen of the inner tube 11 a valve comprising a valve element 16 may be arranged. The fluid line of the connector 12, e.g. the tube 7, comprises a means 13, e.g. a central pole, for opening the valve by displacing the valve element 16. Thus, the valve is opened only after the connection of the connector 12 to the machine connector 30 of the blood treatment device. Thus, spilling of fluid from the connector elements 9 or fluid lines is avoided.

To connect the blood treatment device to the concentrate container, the first part 27 of the machine connector 30 is moved downwards towards the connector 12 until the fluid line/connector element 9 is inserted therein and opens a closing element present on the fluid line/tube of the connector 12.

The connector 12 is affixed to the second part 29. The second part 29 comprises attachment means to that the connector 12 may be affixed via its attachment means 21. The attachment means of the second part 29 can be for example recesses (such as the recesses 31) or protrusions (such as the protrusions 32). These attachment means are preferably fixedly and non-movably connected to the blood treatment device 26.

Between treatment sessions, the connector elements 9 of the blood treatment device 26 need to be rinsed or disinfected. For this purpose, the connector elements 9 of the first part 27 are inserted into the recesses 31 of the second part 29 until the lumen of the outer tube 10 is fluidically closed. The inner tube 11 is arranged retracted into the lumen of the outer tube 10 and thus can be rinsed in this position, because the connector element 9 is fluidically short-circuited.

In this case, rinsing fluid is provided via the lumen of the inner tube 11 and removed to a drain via the lumen of the outer tube 10. Each rinsing recess 31 may be equipped with a structure for actuating a valve to allow the flow of rinsing fluid. These valve actuators can have the shape of central poles 34 (see FIG. 26). In addition to that, the rinsing recesses 31 can be equipped with a drain to remove remaining rinsing fluid.

FIG. 25 shows a different machine connector 30 of a blood treatment device 26 the first part 27 thereof is translationally movable. In FIG. 25 the rinsing recesses 31 in the second part 29 of the machine connector 30 can be seen. A connector 12 can be affixed to the second part 29 by insertion of the attachment elements 21 into the rinsing recesses 31 and the first part 27 comprising the connector element 9 is subsequently moved downwards to establish a fluid connection between the blood treatment device and the concentrate container through the connector 12.

FIG. 26 shows a connector 12 of a concentrate container attached to a blood treatment device 26 via its attachment elements 21. The second part 29 of the machine connector of the blood treatment device 26 comprises a movable drawer 33 comprising the rinsing recesses 31. It is also possible to arrange the rinsing recesses 31 in a fixed position relative to the blood treatment device 26. The movable drawer 33 further comprises attachment elements 32 that are pole-shaped.

The connector 12 comprises attachment elements 21 that have the shape of curved arms configured to receive the corresponding attachment elements 32 of the blood treatment device that are pole-shaped. In the embodiment shown in FIG. 26 the connector is thus not affixed to the blood treatment device via the rinsing recesses 31 but via separate attachment elements 32 and 21 that interact with each other.

Upon connection of the connector 12 to the movable drawer 33 of the second part 29, the movable drawer 33 is then moved towards the blood treatment device 26.

The invention claimed is:

1. A closing element for a fluid line comprising:

a closing portion configured to be arranged on a rim of an open portion of the fluid line, the rim defining an opening at an end of the fluid line, the closing portion further configured to cover the opening to fluidically close the fluid line, wherein the closing portion comprises an intended breaking point;

a main body that extends downward from the closing portion, the main body configured to at least partially receive and surround an outer surface of the fluid line at the end, such that the closing element covers the end of the fluid line and forms a layered structure of the main body and the fluid line when the end of the fluid line is at least partially received and surrounded by the main body; and a pressure receiving portion configured to receive pressure applied by a pressure exertion element, wherein the closing element has a shape of a cap, the pressure receiving portion comprises at least one protrusion that is configured to come into contact with the pressure exertion element.

2. The closing element according to claim 1, wherein the pressure receiving portion comprises an annular protrusion running at least along a part of or along an entire length of an outer circumference of the closing element.

3. The closing element according to claim 1, wherein the closing portion comprises a plurality of plates that are separated from each other by the intended breaking point, the main body comprises a polygonal shape, and a number of the plurality of plates corresponds to a number of edges of the polygonal shape.

4. The closing element according to claim 3, wherein the at least two plurality of plates are arranged at an angle relative to each other.

5. The closing element according to claim 1, wherein the pressure receiving portion comprises a plurality of protrusions arranged along an outer circumference of the closing element.

6. The closing element according to claim 5, wherein each protrusion of the plurality of protrusions is arranged on a respective plate of a plurality of plates forming the closing portion so that pressure applied to each protrusion is selectively transferred to the respective plate the protrusion is arranged on.

7. The closing element according to claim 1, wherein the pressure receiving portion and/or at least one protrusion thereof is present on at least half of a longitudinal length of the closing element in an insertion direction of the fluid line into the closing element.

8. The closing element according to claim 1, wherein the pressure receiving portion and/or at least one protrusion thereof at least partially defines a distal end face of the closing element in the insertion direction of the fluid line into the closing element.

9. The closing element according to claim 1, wherein the main body has a cylindrical or polygonal form.

10. The closing element according to claim 1, wherein at a connection point between the closing portion comprising the intended breaking point and the main body of the closing element the material is selectively weakened, by providing at least one recess, to facilitate breaking of the intended breaking point due to pressure being applied to the pressure receiving portion.

11. The closing element according to claim 1, wherein the closing element is at least partially or completely manufactured from linear low density polyethylene and/or high density polyethylene.

12. The closing element according to claim 1, wherein the closing element is formed from at least two polymers, one of which being easier to break than the other, the polymer being easier to break forming the intended breaking point.

13. A connector comprising at least one fluid line providing a flow path through the connector, wherein the closing element according to claim 1 is arranged on at least one fluid line of the connector to fluidically close the fluid line.

14. The connector according to claim 13, wherein the fluid line comprises only one lumen or an inner lumen and an outer lumen, wherein the closing element is arranged on an end face of the one lumen or the outer lumen and an end face of the inner lumen is arranged retracted into the outer lumen so that a gap is present between the end face of the inner lumen and the closing element.

15. The connector according to claim 13, wherein at least one of the fluid lines of the connector comprises a sharp or pointed leading edge pointing away from the connector.

16. A system comprising the closing element according to claim 1, a connector, and a pressure exertion element, wherein the pressure exertion element is configured to be fluidically connected to the fluid line of the connector by breaking the intended breaking point of the closing element, by a relative movement of the pressure exertion element and the connector.

17. The system according to claim 16, wherein the connector, that is a connector of a concentrate container, and/or the pressure exertion element, that is a connector element of a blood treatment device or a dosing unit thereof, comprises at least one fluid line comprising an inner lumen and an outer lumen arranged concentrically to each other.

18. The closing element of claim 1, wherein the fluid line is a fluid line of a concentrate container, and the connector is a connector element to be fluidically connected to the fluid line by breaking the intended breaking point, and the at least one protrusion projects outwards from the closing portion or the main body that is configured to come into contact with the connector element.

19. The closing element according to claim 1, wherein the at least one protrusion is an annular protrusion running at least along a part of or along an entire length of an outer circumference of the closing element and the main body thereof.

20. The closing element according to claim 1, wherein the at least one protrusion is a plurality of protrusions arranged along an outer circumference of the closing element at the pressure receiving portion thereof, wherein the plurality of protrusions are separate from another and/or arranged in equal intervals along the outer circumference.

* * * * *